(12) United States Patent
Dombrowski et al.

(10) Patent No.: US 9,775,977 B2
(45) Date of Patent: *Oct. 3, 2017

(54) LIQUID APPLICATOR

(71) Applicant: 3M INNOVATIVE PROPERTIES COMPANY, Saint Paul, MN (US)

(72) Inventors: Alan R. Dombrowski, Woodbury, MN (US); Jason L. Aveldson, Prior Lake, MN (US)

(73) Assignee: 3M INNOVATIVE PROPERTIES COMPANY, Saint Paul, MN (US)

(*) Notice: Subject to any disclaimer, the term of this patent is extended or adjusted under 35 U.S.C. 154(b) by 423 days.

This patent is subject to a terminal disclaimer.

(21) Appl. No.: 14/396,470

(22) PCT Filed: Apr. 10, 2013

(86) PCT No.: PCT/US2013/035881
§ 371 (c)(1),
(2) Date: Oct. 23, 2014

(87) PCT Pub. No.: WO2013/162882
PCT Pub. Date: Oct. 31, 2013

(65) Prior Publication Data
US 2015/0094640 A1    Apr. 2, 2015

Related U.S. Application Data

(60) Provisional application No. 61/638,293, filed on Apr. 25, 2012.

(51) Int. Cl.
A61F 13/40      (2006.01)
A61M 35/00     (2006.01)

(52) U.S. Cl.
CPC ........ *A61M 35/006* (2013.01); *A61M 35/003* (2013.01)

(58) Field of Classification Search
CPC combination set(s) only.
See application file for complete search history.

(56) References Cited

U.S. PATENT DOCUMENTS

| 3,757,782 A | 9/1973 | Aiken |
| 3,891,331 A | 6/1975 | Avery |
| 4,183,684 A | 1/1980 | Avery, Jr. |
| 4,528,268 A | 7/1985 | Andersen |
| 4,542,012 A | 9/1985 | Dell |
| 4,584,192 A | 4/1986 | Dell |

(Continued)

FOREIGN PATENT DOCUMENTS

| JP | 2005-246191 | 9/2005 |
| WO | WO 02-46089 | 6/2002 |
| WO | WO 2015/042021 | 3/2015 |

OTHER PUBLICATIONS

International Search Report for PCT International Application No. PCT/US2013/035881, mailed on Jun. 19, 2013, 3pgs.

*Primary Examiner* — David Walczak
(74) *Attorney, Agent, or Firm* — 3M Innovative Properties Company; Lynn R. Hunsberger (57) ABSTRACT

Liquid applicators for applying a liquid to a surface. The applicators include a lever having a hinge, grip and foot integrally formed with a hollow body suitable for receiving a liquid-filled ampoule. The foot is positioned adjacent the ampoule and crushes the ampoule when the lever is depressed.

6 Claims, 4 Drawing Sheets

(56) References Cited

U.S. PATENT DOCUMENTS

| | | |
|---|---|---|
| 4,925,327 A | 5/1990 | Wirt |
| 4,957,385 A | 9/1990 | Weinstein |
| 4,962,562 A | 10/1990 | Englund |
| 5,007,128 A | 4/1991 | Englund |
| 5,098,297 A | 3/1992 | Chari |
| 5,120,301 A | 6/1992 | Wu |
| 5,288,159 A | 2/1994 | Wirt |
| 5,308,180 A | 5/1994 | Pournoor |
| 5,312,197 A | 5/1994 | Abramson |
| 5,396,737 A | 3/1995 | Englund |
| 5,435,660 A | 7/1995 | Wirt |
| 5,445,462 A | 8/1995 | Johnson |
| 5,538,353 A | 7/1996 | DeHavilland |
| 5,658,084 A | 8/1997 | Wirt |
| D386,849 S | 11/1997 | Dehavilland |
| 5,690,958 A | 11/1997 | McGrath |
| 5,752,363 A | 5/1998 | Edwards |
| 5,769,552 A | 6/1998 | Kelley |
| 5,772,346 A | 6/1998 | Edwards |
| 5,775,826 A | 7/1998 | Miller |
| D396,911 S | 8/1998 | Dehavilland |
| 6,299,377 B1 | 10/2001 | Emerit |
| 6,340,097 B1 | 1/2002 | D'Alessio |
| 6,478,191 B1 | 11/2002 | D'Alessio |
| 6,488,428 B1 | 12/2002 | Fischer |
| 6,536,975 B1 | 3/2003 | Tufts |
| 6,729,786 B1 | 5/2004 | Tufts |
| 6,910,822 B2 | 6/2005 | Hidle |
| 6,991,393 B2 | 1/2006 | Tufts |
| 6,991,394 B2 | 1/2006 | Tufts |
| 7,182,536 B2 | 2/2007 | Tufts |
| 7,201,577 B2 | 4/2007 | Levine |
| 7,241,065 B2 | 7/2007 | Tufts |
| 7,834,122 B2 | 11/2010 | Ferenz |
| 2002/0076255 A1 | 6/2002 | Hoang |
| 2004/0179888 A1* | 9/2004 | Tufts ............... A45D 34/04 401/133 |
| 2004/0254561 A1 | 12/2004 | Stenton |
| 2007/0231051 A1* | 10/2007 | Flores ............ A61M 35/006 401/132 |
| 2007/0248399 A1 | 10/2007 | Tufts |
| 2007/0253909 A1 | 11/2007 | Magallon |
| 2007/0254854 A1 | 11/2007 | Magallon |
| 2008/0108674 A1 | 5/2008 | Magallon |
| 2008/0219750 A1 | 9/2008 | Siegel |
| 2008/0292383 A1 | 11/2008 | Tufts |
| 2008/0298879 A1 | 12/2008 | Chesak |

* cited by examiner

LIQUID APPLICATOR

CROSS REFERENCE TO RELATED APPLICATIONS

This application is a national stage filing under 35 U.S.C. 371 of PCT/US2013/035881, filed 10 Apr. 2013, which claims priority to U.S. Provisional Application No. 61/638,293, filed 25 Apr. 2012, the disclosures of which are incorporated by reference in their entirety herein.

FIELD

The present disclosure relates to a liquid applicator for applying a liquid to a surface, e.g., a surgical prep applicator. In particular, the present disclosure relates to a liquid applicator having a lever suitable for crushing an ampoule and releasing liquid within the applicator.

SUMMARY

Briefly, in one aspect, the present disclosure provides a liquid applicator for applying a liquid to a surface. Generally, the applicator comprises an elongated hollow body comprising a wall defining an internal chamber having a closed end and an open end; wherein the wall comprises a handle region and a crush region and wherein the ratio of thickness of the wall in the crush region over the thickness of the wall in the handle region is less than 1. A first ampoule formed of a frangible material is located in the internal chamber proximate the crush region and containing the liquid. A lever is integral with the hollow body and comprises a hinge projecting from a first location attached to the hollow body to a second location, a grip extending from the second location to a third location, and a foot integral to the wall adjacent the crush region. The lever comprises a first truss extending from the third location to the foot; a third truss extending from the second location to the foot, and a second truss between the first and third trusses and extending from the foot to a fourth location, between the second and third location. The width of the first truss is tapered from a first width proximate the third location and a second width proximate foot; wherein the ratio of the second width over the first width is less than 1.

In some embodiments, the width of the third truss is tapered from a third width proximate the second location to a fourth width proximate the foot; wherein the ratio of the fourth width over the third width is less than 1. In some embodiments, the second truss projects substantially perpendicular to the major axis of the elongated hollow body.

In some embodiments, the liquid applicator further comprises a pad connected to the open end of the hollow body. In some embodiments, the pad comprises a series of alternating peaks and troughs repeating across the exposed surface of the pad.

The above summary of the present disclosure is not intended to describe each embodiment of the present invention. The details of one or more embodiments of the invention are also set forth in the description below. Other features, objects, and advantages of the invention will be apparent from the description and from the claims.

BRIEF DESCRIPTION OF THE DRAWINGS

FIG. 6b illustrates a side view of the exemplary pad of FIG. 6a.

DETAILED DESCRIPTION

Antiseptic preparation of patient's skin for surgery conventionally includes a 3-10 minute scrubbing of the affected area with an antiseptic soap solution followed by the application of a water-soluble antiseptic paint solution. These solutions have been applied with saturated sponges that are attached to a blade or held with forceps. These sponges are often saturated by soaking them in open pans of solution. Sometimes, sponges with attached handles are provided in a plastic or aluminum foil laminate pouch containing enough liquid to saturate the sponges. In some products the sponges are supplied dry in a sterile "kit" with the antiseptic solutions provided in relatively thin walled 4 oz. polyethylene bottles. These bottles generally have wall thickness less than about 500 microns. While inexpensive, these techniques are messy and offer little control over inadvertent dripping of the solution into areas where it is undesired.

Alternatively, devices have been developed in an attempt to prevent solution dripping associated with these techniques, and to reduce the time required for application of the antiseptic solution. For example, liquid applicators that hold the liquid in a frangible ampoule and require additional elements to crush the ampoule and release the liquid have been developed. However, existing applicators are often complex to construct and may be difficult or cumbersome to use.

For example, some liquid applicators use a multipart design. Such liquid applicators include an elongated hollow body containing frangible ampoule that holds a liquid. A hinge is integrally formed with and projects from the outer wall of the hollow body. A separately formed part having a grip and a foot is attached to the hinge. If properly designed, when the grip is pressed, it will rotate about the hinge, causing the foot to compress the hollow body and fracture the ampoule releasing the liquid. Generally, the liquid then flows from the chamber to be applied to the desired surface.

By manufacturing the lever separate from the hollow body, different materials may be used to achieve the desired results. For example, typically the hollow body is formed of a flexible, low modulus material such as low density polyethylene. In contrast, the lever is typically formed of a more rigid, higher modulus material such as high density polyethylene or polycarbonate. With such selections, the force applied to lever will be sufficient to compress the hollow body and fracture the ampoule before the lever itself is significantly deformed. However, such a two-part structure is more complex to manufacture.

Other liquid applicators use a one-part design. Here, a lever is integrally formed with the hollow body. The lever includes a hinge, a grip, and a foot. If properly designed, when the grip is depressed, it will rotate about the hinge, causing the foot to compress the hollow body and fracture the ampoule releasing the liquid. The integral design of such applicators is simpler to construct; however, only a single material can be used for the entire construction. In such prior art applicators, rigid, high modulus materials have been chosen to ensure the force applied to lever will be sufficient to compress the hollow body and fracture the ampoule before the lever itself is significantly deformed. This requirement has led to designs that include the use of awkward and less efficient non-cylindrical hollow body designs. Even with such modifications, these applicators may be difficult to operate.

Figure 1:
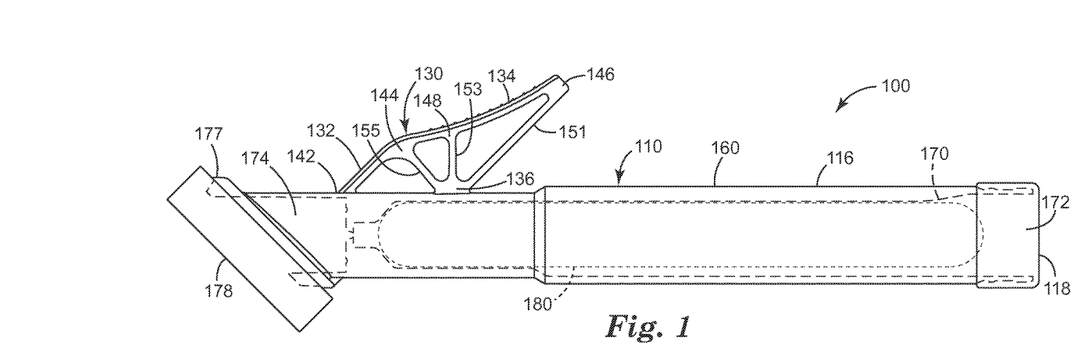
FIG. 1 illustrates a side view of one exemplary liquid applicator according to some embodiments of the present disclosure.

An exemplary liquid applicator according to one embodiment of the present disclosure is illustrated in FIG. 1. Liquid applicator 100 comprises elongated hollow body 110 comprising wall 160. Wall 160 defines chamber 170 having closed end 172 and open end 174. Closed end 172 may be sealed in any of a variety of known ways to inhibit or prevent fluid contained within the chamber from escaping through the closed end. For example, cap 118, which may be press-fit, screwed or otherwise attached, may seal the chamber forming closed end 172.

Open end 174 allows fluid to flow from the hollow body and be applied where desired. In some embodiments, pad 178 may be attached to the open end to control the flow rate and distribution of the fluid. Pad 178 may be formed of any suitable, porous substance including, e.g., sponge, woven and nonwoven materials, screens, meshes and combinations thereof. A wide variety of known materials can be used in the construction of the pad including, e.g., polyester polyurethane and polyester polyether open cell foams.

In some embodiments, such as the one shown in FIG. 1, open end 174 terminates in flange 177, which provides a mating surface for pad 178. In addition, flange 177 may include features such as ribs, holes, and channels to aid in the control and distribution of the flow. The pad can be attached to the flange by known means including, e.g., adhesives and ultrasonic welding.

Ampoule 180 is located within chamber 170. Generally, the ampoule is formed of a frangible material, e.g., glass. Such materials are relatively brittle and will fracture when compressed. This is in contrast to relatively flexible materials that would deform when compressed but which must be punctured to release the liquid inside. In some embodiments, score lines or other features that provide local areas of weakness in the frangible material may be included to control breaking and/or reduce the force required to break the ampoule.

The size and shape of the ampoule is selected to be compatible with the dimensions of the internal chamber and the desired volume of liquid. For example, for use in preparation for a small surgical procedure, the amount of liquid in the ampoule should generally be sufficient to cover an area of, e.g., 10 square centimeters or more. For larger surgical procedures, the amount of liquid in the ampoule may need to be sufficient to cover at least the torso of a large person, e.g., at least about 500-600 square centimeters.

Ampoule 180 contains the liquid to be dispensed. Generally, any liquid can be contained within the ampoule, with the selection of the liquid influencing the selection of the materials used to construct the ampoule and other parts of the applicator, as understood by one of ordinary skill in the art. In some embodiments, the applicator may be particularly useful in dispensing liquids having viscosities at room temperature of less than about 10,000 cps, most preferably less than about 500 cps.

In some embodiments, the ampoule may contain an antiseptic preparation. Examples of suitable antiseptic preparations include those described in U.S. Pat. No. 4,584,192 and those described in U.S. Pat. No. 4,542,012. Other useful fluids include antiseptic preparations, e.g., iodophoric skin tinctures, such as "Duraprep™ Surgical Solution," commercially available from 3M. In some embodiments, the ampoule be filled with a composition that includes an antimicrobial agent such as iodine, an iodine complex (e.g., iodophors), chlorhexidine, chlorhexidine salts (e.g., chlorhexidine digluconate and chlorhexidine diacetate), or combinations thereof. Other exemplary antimicrobial agents include C2-C5 lower alkyl alcohols, fatty acid monoesters of glycerin and propylene glycol, polymers that include a (C12-C22) hydrophobe and a quaternary ammonium group, polyquaternary amines (e.g., polyhexamethylene biguanide), quaternary ammonium silanes, silver, silver salts (such as silver chloride), silver oxide and silver sulfadiazine, methyl, ethyl, propyl and butyl parabens, octenidene, peroxides (e.g., hydrogen peroxide and benzoyl peroxide), and the like, as well as combinations thereof.

Liquid applicator 100 also comprises lever 130 comprising hinge 132, grip 134, and foot 136. Hinge 132 extends from first location 142, which is integral to hollow body 110, to second location 144. Grip 134 continues the lever from second location 144 to third location 146. Trusses 151, 153, and 155 connect hinge 132 and grip 134 to foot 136. First truss 151 extends from third location 146 to foot 136. Similarly, third truss 155 extends from second location 144 to foot 136. Second truss 153 is located between the first and third truss and extends from foot 136 to grip 134 at fourth location 148, which is between the second and third locations.

Figure 2:
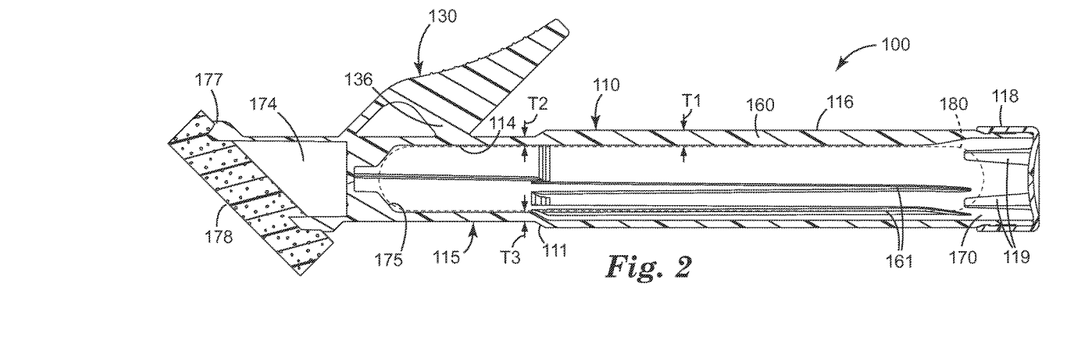
FIG. 2 illustrates a cross section of the exemplary liquid applicator of FIG. 1.

Additional features suitable for use in some embodiments are shown in FIG. 2, which illustrates a cross section of the exemplary applicator 100 of FIG. 1. For example, cap 118, which is press-fit onto hollow body 110, includes optional prongs 119 which conform to the end of ampoule 180 holding in place. Wall 160 includes optional ribs 161 projecting into chamber 170 aiding in the placement and retention of ampoule 180. Hollow body 160 may also include optional stop 175. In some embodiments, when an ampoule is inserted in the chamber, it is seated against the stop helping to position the ampoule relative to the lever. Although not shown, in some embodiments, a screen or other filtering means may be located near open end 174 preventing shards of the crushed ampoule from reaching pad 178.

Hollow body 110 includes handle 116 which can be manually gripped during use. Here, wall 160 has first thickness, T1. In crush region 114, located adjacent foot 136, wall 160 has second thickness, T2, which is less than first thickness, T1. Hollow body 110 may include optional step 111 transitioning between handle 116 and crush region 114.

Generally, first thickness, T1, is selected to provide the desired mechanical integrity and may depend on known factors such as the choice of material and the design of the applicator. For example, for a given material, the wall should be of sufficient thickness to prevent crushing the ampoule when the handle is gripped during normal use. In addition, the thickness should be sufficient to prevent shards of the broken ampoule from penetrating the wall. Generally, first thickness T1 is at least 1 mm, e.g., at least 2 mm. In some embodiments, thickness T1 is no greater than 5 mm, e.g., no greater than 4 mm.

Generally, second thickness, T2, is selected to reduce the force required to deform the wall in crush region 114. As the applicator is often operated with a single hand, the grip is depressed by thumb. Given the wide range of thumb strength for potential operators, it can be desirable to minimize the force required to depress the grip, compress the wall, and fracture the ampoule. However, the second thickness should still be adequate to minimize or prevent unintended crushing and to retain any shards of broken ampoule. Generally, the ratio of T2 over T1 is less than 1. In some embodiments, the ratio of T2 over T1 is no greater than 0.9, no greater than 0.7, or even no greater than 0.5. In some embodiments, the ratio of T2 over T1 is at least 0.2, in some embodiments, at least 0.4.

Generally, the length of crush region 114 should be longer than the length of foot 136. In some embodiments, crush region extends from handle 116 to a location near or at open end 174. In some embodiments, crush region 114 may end at stop 175.

In some embodiments, the crush region may extend throughout the circumference of the applicator. However, in some embodiments, the walls may not be thinned throughout the circumference of the hollow body. For example, in some embodiments, the wall in support region 115 may be thicker than in crush region 114. In some embodiments, the wall in support region 115 may have a third thickness, T3, which is greater than the fist thickness, T1. In some embodiments, the ratio of T3 over T1 is at least 1.1, e.g., at least 1.2, or even at least 1.3. Generally, the circumferential width of the crush region should be greater than the width of the foot. In some embodiments, the crush region extends at least +/−30 degrees from the foot, in some embodiments, at least +/−60 degrees, or even +/−90 degrees. Generally the support region would encompass the remaining circumference of the hollow body.

Figure 3:
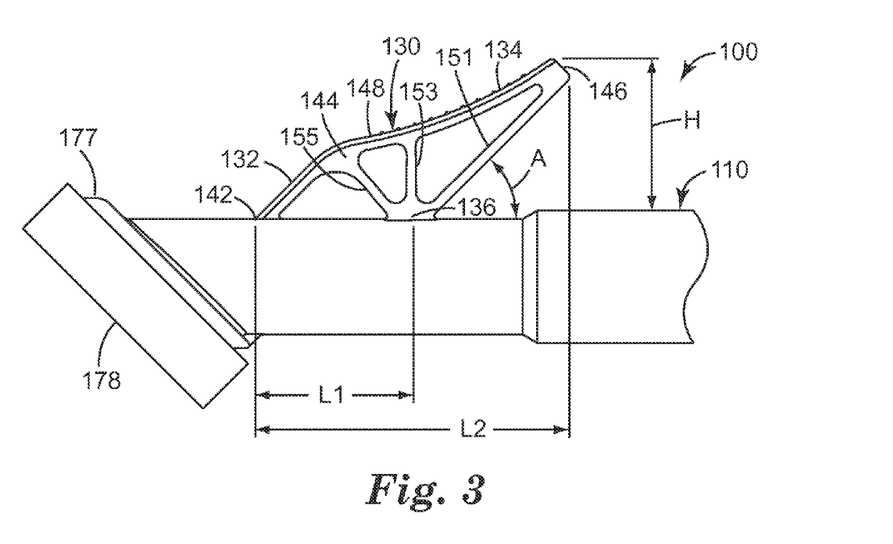
FIG. 3 illustrates a side view of one exemplary lever corresponding to the lever of the exemplary liquid applicator of FIG. 1.

A larger view of exemplary lever 130 is shown in FIG. 3. Hinge 132 connects to and is integral with hollow body 110 at first location 142. The hinge extends from the hollow body at an angle terminating at second location 144 corresponding to the location of third truss 155. Grip 134 continues the lever from second location 144 to third location 146 at a distance H from the hollow body. Foot 136 is connected to, and integral with hollow body 110. First truss 151 extends from third location 146 to foot 136 forming angle A with wall 160.

Figure 4A:
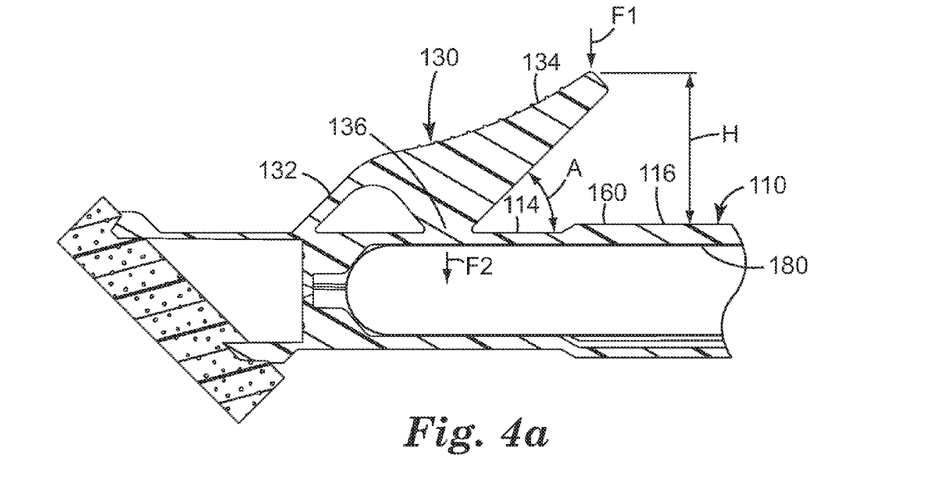
FIG. 4a illustrates a cross section of the exemplary lever of FIG. 3, before crushing.
Figure 4B:
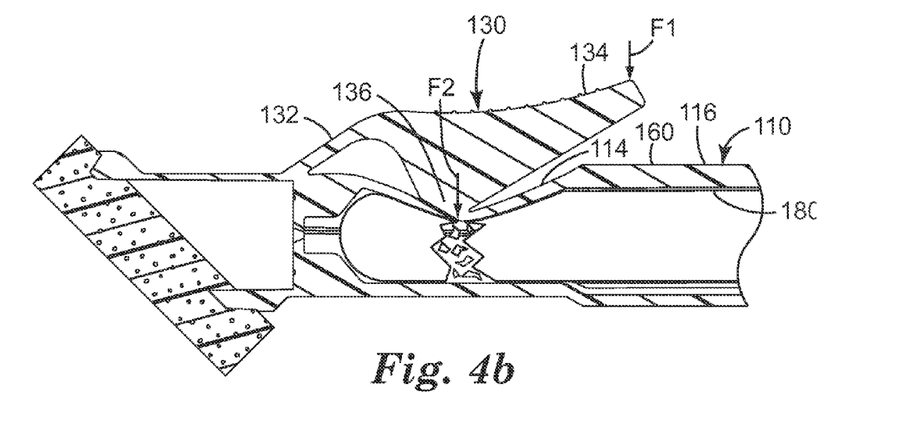
FIG. 4b illustrates a cross section of the exemplary lever of FIG. 3, after crushing.

While there is some flexibility in the design of the lever, the present inventors have discovered certain dimensions which are important to ease of use and functionality. FIG. 4a illustrates a cross section of the lever of FIG. 3, showing its position before crushing ampoule 170. FIG. 4b illustrates a cross section of the lever of FIG. 3, showing its position after crushing ampoule 170 producing shards 171. Angle A and height H should be selected such that when grip 134 is depressed, the travel of foot 136 is sufficient to compress wall 160 in crushing region 114 and fracture ampoule 170 before grip 134 contacts wall 160 in handle region 116. By increasing the angle A, sufficient distance H can be achieved without requiring a grip of unwieldy length. In some embodiments, angle A is greater than 30 degrees, e.g., greater than 40 degrees. If angle A is too steep, however, it may be difficult to actuate the lever. In some embodiments, angle A is no greater than 60 degrees, e.g., no greater than 50 degrees.

Distance, H, will be somewhat dependent on the diameter of the chamber and ampoule, as the foot, and therefore the grip, must be capable of travelling a sufficient distance in order to crush the ampoule. In some embodiments, H is greater than 0.5 times the diameter of the chamber, e.g., at least 1 times the diameter of the chamber, or even at least 1.5 times the diameter of the chamber. In some embodiments, height H is at least 10 mm, e.g., at least 20 mm. In some embodiments, height H is no greater than 40 mm, e.g., no greater than 30 mm.

When grip 134 is depressed with applied force F1, lever 130 operates as a second degree lever applying a crushing force F2 at foot 136. Crushing force F2 can be enhanced relative to applied force F1 by appropriate selection of lengths L1 and L2. L1 is the distance between first location 142 where hinge 132 is connected the wall and the center of foot 136. L2 is the distance from first location 142 to third location 146 at the end of grip 134. Generally, the ratio of F2 over F1 is proportional to the ratio of L2 over L1. In some embodiments, the ratio of L2 over L1 is at least 1.5, e.g., at least 1.8. In some embodiments, the ratio of L2 over L1 is no greater than 3, e.g., no greater than 2.5.

In order to concentrate the crushing force and reduce the applied force required to break ampoule 170, it may be desirable to decrease the size of foot 136. However, if the area of foot 136 is too small, lever 130 may flex to the side when compressed hindering operation. This problem has been reduced in prior art constructions through the use of rigid, high modulus materials. However, alternative approaches are required when flexible, lower modulus materials are used. Referring to FIG. 3, second truss 153 assists in transferring force to foot 136, and along with trusses 151 and 155 aides in stabilizing the lever. In some embodiments, second truss 143 extends substantially perpendicularly from wall 160. For example, in some embodiments second truss 143 forms an angle of between 80 and 100 degrees, in some embodiments, between 85 and 95 degrees relative to wall 160. In some embodiments, two or three of the trusses may merge at a common location at the foot. Alternatively, as shown in FIG. 3, in some embodiments, each of the trusses may connect to foot 136 at spaced-apart locations providing further stability to the lever.

Figure 5:
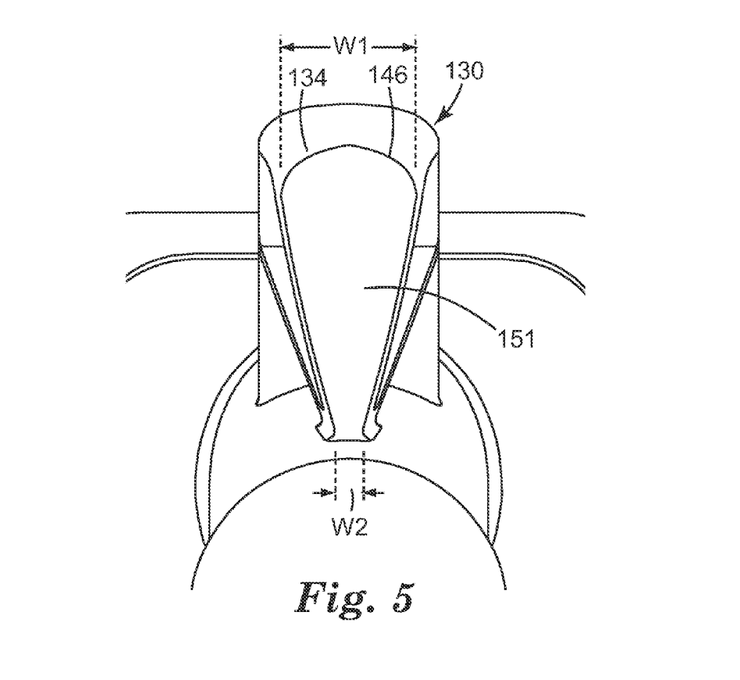
FIG. 5 illustrates an end view of the exemplary lever of FIG. 3.

An end view of lever 130 according to some embodiments of the present disclosure is shown in FIG. 5. The top of grip 134 has a first width W1 where it terminates at third location 146. Generally, the top surface of grip 134, including its width, is selected to provide a comfortable and stable base form the application of force to crush the ampoule. In general, the size may be selected to correspond to the expected range of widths of the human thumb. In some embodiments, width W1 is at least 5 mm, e.g., at least 10 mm. In some embodiments, width W1 is no greater than 25 mm, e.g., no greater than 20 mm.

In some embodiments, in order to further concentrate the applied force onto foot 136, first truss 151 may be tapered. That is, the width of first truss 151 may decrease from first width W1 where the truss connects to the grip to second width W2 where the truss connects to foot 136. Generally, the ratio of W2 over W1 is less than 1, e.g., less than 0.8, less than 0.5 or even less than 0.4. The minimum desirable width at foot 136 will be influenced by the desirable stability of the lever, as the narrower the foot the more likely undesirable sidewise flexing may occur. In some embodiments, width W2 is at least 2 mm, e.g., at least 3 mm. In some embodiments, width W2 is no greater than 6 mm, e.g., no greater than 5 mm.

Along with its width, the length of foot 136 determines the pressure applied to crush the ampoule, with a smaller foot creating more pressure per unit force applied. However, as with the width, mechanical robustness and lever stability affect the minimum foot length. In some embodiments, the length of the foot is at least 3 mm, e.g., at least 5 mm. In some embodiments, the length of the foot is no greater than 12 mm, e.g., no greater than 10 mm, or even no greater than 8 mm.

A wide variety of pads are known, including sponges and fabrics. Generally, such pads have been cylindrical or rectangular in shape with substantially smooth surfaces, i.e., although the surface may have some small scale roughness associated with the material selected, no large scale variations in the thickness of the applicator are present. All such applicators are suitable for use in the various embodiments of the present disclosure. However, in some embodiments, the present inventors have discovered that an undulating pad may provide additional benefits in the uniform application of liquids to surfaces.

Figure 6A:
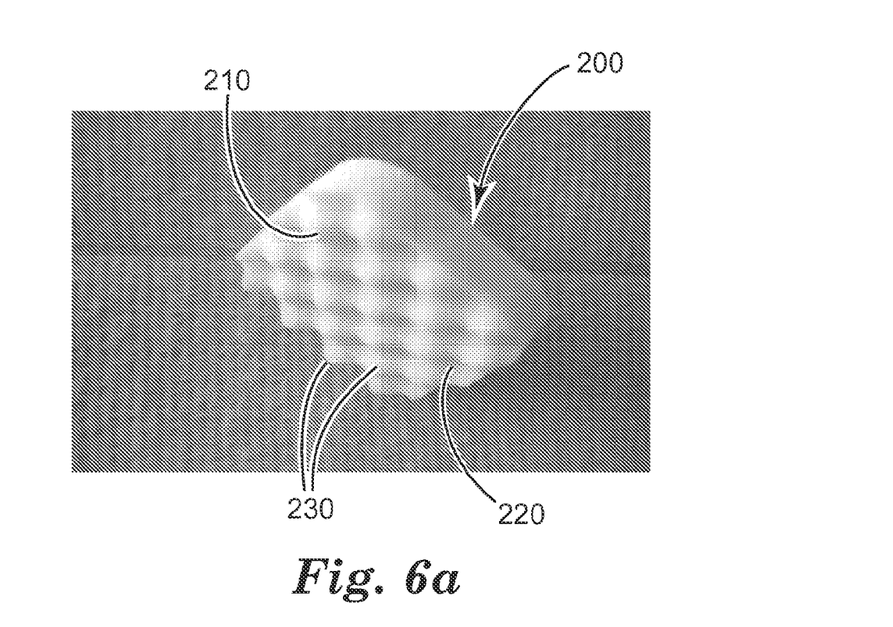
FIG. 6a is an image of an exemplary pad according to some embodiments of the present disclosure.
Figure 6B:
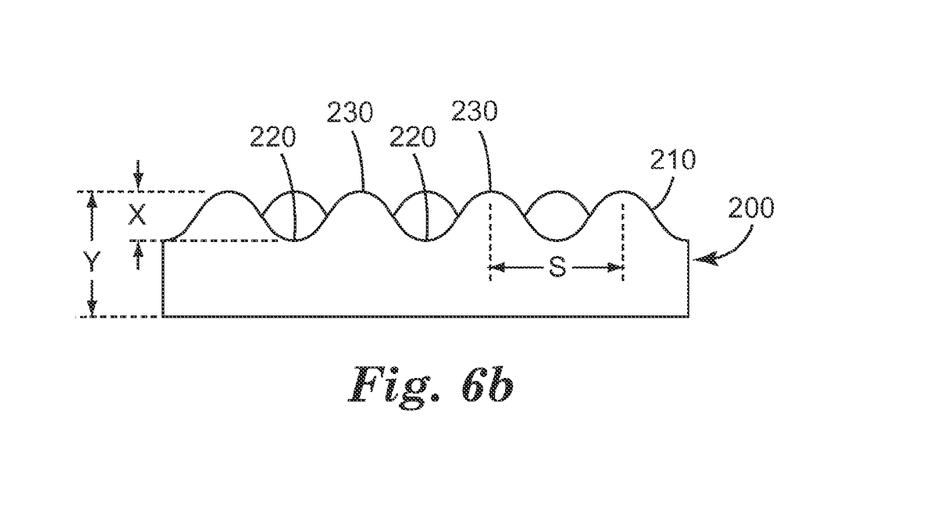

An exemplary pad 200, suitable for use in some embodiments of the present disclosure is shown in FIGS. 6a and 6b. Pad 200 is formed of a sponge, although any material or combination of materials known for use in applicators may be used. Pad 200 generally has a rectangular perimeter with rounded corners. However, any suitable shape may be used, e.g., diamond, circular, oval or iron shaped. Pad 200 differs from pads commonly used with applicators in that exposed surface 210 includes a series of troughs 220 and peaks 230. Thus, although the density of the foam is substantially uniform, the height and available fluid bearing volume of the foam varies across the surface of the pad.

The present inventors have discovered that such a combination of features provides greater control over the delivery and uniformity of the applied liquid. For example, as greater pressure is applied between the applicator and the surface, more of the applicator will contact the surface and the enhance pressure will deliver more fluid. As the application pressure is reduced, and the undulations are released from compression, fluid can be wicked into the sponge aiding in the prevention of pooling and over delivery of fluid. In addition, at lower pressures, the contact area between the applicator and the surface consists of discrete contact regions. Thus, as the applicator is repeated passed over a surface, the fluid is more readily spread rather than being removed or re-absorbed into the pad as can occur with a continuous contact surface.

A side view of pad 200 is shown in FIG. 6b. Surface 210 includes a matrix of peaks 230 and troughs 220. Generally, the height and spacing of the peaks can be varied. In some embodiments, the ratio of peak to trough height, X, over the total pad thickness Y is less than 0.6, e.g., less than 0.5. In some embodiments, the ratio of X over Y is at least 0.1, e.g., at least 0.2, or even at least 0.3. Generally, the peak to trough height X may be uniform or non-uniform and can vary across the surface of the pad. In some embodiments, the average peak to trough height is at least 1 mm, e.g., at least 2 mm. In some embodiments, the maximum average peak to trough height is less than 6 mm, e.g., less than 5 mm. In some embodiments, the average total pad thickness, Y, is at least 5 mm, e.g., at least 8 mm. In some embodiments, the average total pad thickness is no greater than 15 mm, e.g., no greater than 10 mm.

Generally, the spacing of the peaks can be uniform or non-uniform across the surface of the applicator. In some embodiments, the peak to peak spacing, S, is comparable to the peak to trough height X. For example, in some embodiments, the ratio of S over H is between 0.7 and 1.3, inclusive, e.g., between 0.8 and 1.2, or even between 0.9 and 1.1. In some embodiments, the peaking spacing is greater than the peak to trough height. For example, in some embodiments, the ratio of S over H is at least 2, e.g., at least 3, or even at least 4. In some embodiments, the ration of S over H is no greater than 6, e.g., no greater than 5.

In addition to applying a composition, in some embodiments, applicators of the present disclosure may be used to scrub the surface. Pads having a pattern of peaks and troughs across the surface of the pad, such as those illustrated in FIGS. 6a and 6b may be advantageous for scrubbing. The peaks allow greater force concentration to deliver a scrubbing action, while the troughs minimize removal of the antiseptic during scrubbing. In addition, a uniform pattern of peaks and troughs allows consistent scrubbing regardless of the direction of linear scrubbing or even in scrubbing is performed with a circular motion. The density and firmness of the pad may be selected to achieve the desired level of scrubbing action without undue surface irritation.

Liquid applicators according to the present disclosure were molded from linear low density polyethylene and high density polyethylene. The required crush force of these unitary structures was compared to the crush force for three commercially available applicators.

Applicators were place in a V-shaped block and held at a 45 degree angle with the pad facing downward. In this orientation, the lever was in an approximately vertical position. A handheld force gauge was held horizontal, and perpendicular to the lever with its sensor contacting the outermost point on the grip. The force gauge was pressed forward to compress the lever and crush the ampoule.

The first commercial product tested was the 8635 DuraPrep™ applicator available from 3M Company, St. Paul Minn. This was a two part construction with the hollow body formed from linear low density polyethylene, and a separate lever formed of a rigid polycarbonate. Based on five tests, the average applied force for this commercial product was 50+/−2 Newtons. Commercial experience indicates that this is an acceptable force.

The second commercial product tested was a 10 mL ChloroPrep™ applicator available from CareFusion. This was a unitary structure formed of high density polyethylene and having two levers positioned on opposite sides of a hollow body. Based on four samples, the average applied force for this commercial product was 41+/−2 Newtons. Commercial experience indicates that this is an acceptable force.

The third commercial product tested was a 26 mL ChloroPrep™ applicator available from CareFusion. This was a unitary structure formed of high density polyethylene and having a single lever attached to the hollow body. The hollow body had an oval cross section housing two ampoules side-by-side such that the lever crushed both ampoules. Based on five samples, the average applied force for this commercial product was 69+/−16 Newtons. Commercial experience indicates that this is a noticeable increase in required force relative to the other commercial products.

Based on seven examples prepared using linear low density polyethylene (flexural modulus of 317 MPa), the average applied force was 45+/−3 Newtons. Based on ten samples prepared using high density polyethylene (flexural modulus of 1070 MPa), the average applied force was 61+/−5 Newtons. Thus, the present disclosure describes one-part applicator designs that, when prepared from low modulus materials, provide comparable performance to two-part designs.

Generally, the applicators of the present disclosure can be made by known methods. In some embodiments, injection molding may be used. A variety of materials may be used to form the applicators. In some embodiments, applicators formed of low flexural modulus materials such as low density polyethylene may be used. For example, in some embodiments, materials having a flexural modulus of no greater than 500 Mpa, e.g., no greater than 400 MPa, or even no greater than 350 MPa may be used.

Various modifications and alterations of this invention will become apparent to those skilled in the art without departing from the scope and spirit of this invention.

What is claimed is:

1. A liquid applicator for applying a liquid to a surface, the applicator comprising:
    an elongated hollow body comprising a wall defining an internal chamber having a closed end and an open end; wherein the wall comprises a handle region and a crush region and wherein the ratio of thickness of the wall in the crush region over the thickness of the wall in the handle region is less than 1;
    a first ampoule formed of a frangible material located in the internal chamber proximate the crush region and containing the liquid;
    a lever integral with the hollow body and comprising a hinge projecting from a first location attached to the hollow body to a second location, a grip extending from the second location to a third location, and a foot integral to the wall adjacent the crush region;
    wherein the lever comprises a first truss extending from the third location to the foot; a third truss extending from the second location to the foot, and a second truss between the first and third trusses and extending from the foot to a fourth location, between the second and third location;
    wherein the width of the first truss is tapered from a first width proximate the third location and a second width proximate foot; wherein the ratio of the second width over the first width is less than 1.

2. The liquid applicator of claim 1, wherein the width of the third truss is tapered from a third width proximate the second location to a fourth width proximate the foot; wherein the ratio of the fourth width over the third width is less than 1.

3. The liquid applicator of claim 1, wherein the second truss projects substantially perpendicular to the major axis of the elongated hollow body.

4. The liquid applicator according to claim 1, wherein the applicator is formed of a material having a flexural modulus of no greater than 500 MPa.

5. The liquid applicator according to claim 1, further comprising a pad connected to the open end of the hollow body.

6. The liquid applicator of claim 5, wherein the pad comprises a series of alternating peaks and troughs repeating across the exposed surface of the pad.

* * * * *

UNITED STATES PATENT AND TRADEMARK OFFICE
CERTIFICATE OF CORRECTION

PATENT NO. : 9,775,977 B2  
APPLICATION NO. : 14/396470  
DATED : October 3, 2017  
INVENTOR(S) : Alan Dombrowski Page 1 of 1

It is certified that error appears in the above-identified patent and that said Letters Patent is hereby corrected as shown below:

In the Specification

<u>Column 4</u>  
Line 19     Delete "octenidene," and insert -- octenidine, --, therefore.

<u>Column 5</u>  
Line 25     Delete "fist" and insert -- first --, therefore.

<u>Column 8</u>  
Line 37     Delete "ChloroPrep™" and insert -- ChloraPrep™ --, therefore.  
Lines 44-45  Delete "ChloroPrep™" and insert -- ChloraPrep™ --, therefore.

Signed and Sealed this  
Twenty-eighth Day of November, 2017

Joseph Matal  
*Performing the Functions and Duties of the*  
*Under Secretary of Commerce for Intellectual Property and*  
*Director of the United States Patent and Trademark Office*